United States Patent
Zheng et al.

(10) Patent No.: US 11,077,214 B2
(45) Date of Patent: Aug. 3, 2021

(54) MULTIMODAL CT/OPTICAL AGENTS

(71) Applicant: University Health Network, Toronto (CA)

(72) Inventors: Jinzi Zheng, North York (CA); David A. Jaffray, Etobicoke (CA); Christine Allen, Toronto (CA)

(73) Assignee: University Health Network, Toronto (CA)

( * ) Notice: Subject to any disclaimer, the term of this patent is extended or adjusted under 35 U.S.C. 154(b) by 301 days.

(21) Appl. No.: 14/892,444

(22) PCT Filed: May 26, 2014

(86) PCT No.: PCT/CA2014/050493
§ 371 (c)(1),
(2) Date: Nov. 19, 2015

(87) PCT Pub. No.: WO2014/186909
PCT Pub. Date: Nov. 27, 2014

(65) Prior Publication Data
US 2016/0095944 A1 Apr. 7, 2016

Related U.S. Application Data

(60) Provisional application No. 61/827,286, filed on May 24, 2013.

(51) Int. Cl.
*A61K 49/04* (2006.01)
*A61K 49/00* (2006.01)

(52) U.S. Cl.
CPC ...... *A61K 49/0466* (2013.01); *A61K 49/0084* (2013.01)

(58) Field of Classification Search
None
See application file for complete search history.

(56) References Cited

U.S. PATENT DOCUMENTS 6,662,040 B1 * 12/2003 Henrichs ............... A61K 41/00
424/9.2
2007/0258908 A1 * 11/2007 Lanza ............... A61K 49/0041
424/9.322

FOREIGN PATENT DOCUMENTS

WO 98/48845 A1 11/1998
WO 2006/084382 A1 8/2006

OTHER PUBLICATIONS

Lian et al. Trends and developments in liposome drug delivery systems. 2001 J. Pharm. Sci. 90: 667-680. (Year: 2001).*
(Continued)

*Primary Examiner* — Jennifer Lamberski
(74) *Attorney, Agent, or Firm* — Leason Ellis LLP

(57) ABSTRACT

The present application relates to compositions comprising an iodinated contrast agent and indocyanine green co-encapsulated inside a liposomal carrier, various uses thereof as well as methods for their preparation.

19 Claims, 15 Drawing Sheets

(56) References Cited

OTHER PUBLICATIONS

Proulx et al. Quantitative imaging of lymphatic function with liposomal indocyanine green. 2010 Cancer Res. 70: 7053-7062. (Year: 2010).*
Extended European Search Report of corresponding European Patent Application No. 14800554.9 dated Nov. 30, 2016.
Huang, Huang et al.,Comparison of Computed Tomography- and Optical Image-Based Assessment of Liposome Distribution, Molecular Imaging, vol. 12, No. 3., May 2013, pp. 148-160.
International Search Report and Written Opinion of corresponding application No. PCT/CA2014/050493 dated Sep. 8, 2014.
Zheng, Jinzi, et al., "Multimodal Contrast Agent for Combined Computed Tomography and Magnetic Resonance Imaging Applications", Investigative Radiology, vol. 41, No. 3, Mar. 2006, pp. 339-348.
Huang, Huang, et al., "Comparison of Computed Tomography-and Optical Image-Based Assessment of Liposome Distribution", Molecular Imaging, vol. 12, No. 3, May 2013, pp. 1-13.
Proulx, Steven T., "Quantitative Imaging of Lymphatic Function with Liposomal Indocyanine Green", Cancer Research, vol. 70, No. 18, Sep. 2010, pp. 7053-7062.
Zheng, Jinzi, et al., "A Novel CT/PET Agent to Characterize Heterogeneity in Intratumoral Distribution of Nanoparticles with Extended Detection Sensitivity Range", Conference, WMIC, Dublin, Sep. 5-8, 2012.
Myhr, Gunnar, "Multimodal Cancer Treatment: Real Time Monitoring, Optimization, and Synergistic Effects", Technology in Cancer Research and Treatment, ISSN 1533-0346, vol. 7, No. 5, Oct. 2008, pp. 409-414.
Bernstein et al. "Improved sensitivity of computed tomography towards iodine and gold nanoparticle contrast agents via iterative reconstruction methods." Scientific Reports 6 (2016): 26177.
Chen et al. "Advance of molecular imaging technology and targeted imaging agent in imaging and therapy." BioMed Research International 2014 (2014).
Frangioni et al. "In vivo tracking of stem cells for clinical trials in cardiovascular disease." Circulation 110.21 (2004): 3378-3383.
Mordon et al. "Indocyanine green: physicochemical factors affecting its fluorescencein vivo." Microvascular Research 55.2 (1998): 146-152.
Van Den Biesen et al. "Yield of fluorescence from indocyanine green in plasma and flowing blood." Annals of Biomedical Engineering 23.4 (1995): 475-481.
Wang et al. "Self-assembled nanomaterials for photoacoustic imaging." Nanoscale 8.5 (2016): 2488-2509.
Zheng et al. "Nanosystems for multimodality in vivo imaging." Multifunctional Pharmaceutical Nanocarriers. Springer, New York, NY, 2008. 409-430.
International Preliminary Report on Patentability in corresponding International Patent Application No. PCT/CA2014/050493 dated Nov. 24, 2015. 7 pages.

* cited by examiner

A

A

F

Preoperative CT imaging

Intraoperative NIR fluorescence imaging

| Region | Mean fluorescence signal (a.u.) | Tumor-to-background signal ratio |
|---|---|---|
| Background | 19.3 ± 1.1 | 1.0 ± 0.0 |
| Tumor (1) | 131.4 ± 2.7 | 6.8 ± 0.4 |
| Tumor (2) | 108.2 ± 8.8 | 5.6 ± 0.6 |

MULTIMODAL CT/OPTICAL AGENTS

CROSS-REFERENCE TO RELATED APPLICATIONS

This application is a National Stage of co-pending International Application No. PCT/CA2014/050493 filed May 26, 2014 which claims the benefit of priority from U.S. provisional application No. 61/827,286 filed on May 24, 2013, the contents of both of which are incorporated herein by reference in their entirety.

FIELD

The present disclosure relates to multimodal liposomal CT/optical contrast agents and to methods for using and manufacturing liposome formulations comprising multimodal imaging agents.

INTRODUCTION

The development of new imaging agents suitable for therapy guidance is a relatively unexplored and yet highly exciting and rewarding research space. Particularly in surgical oncology, where effective screening programs and early diagnosis present surgeons with increasingly challenging cases of patients with small tumors that are non-visible and non-palpable. In addition, tissue-conserving surgeries require accurate identification of the tumor margins, as well as knowledge of lymph node involvement in the operating room.

Lung cancer is the most common form of cancer and is the leading cause of cancer-related deaths in the Western world. Overall survival at five years for lung cancer is approximately 15% and has not significantly improved over the last several decades [1]. A major challenge in the management of lung cancer is that the disease can progress asymptomatically and present itself at advanced stages, which demands for timely and accurate surgical procedures in order to improve patient survival and decrease morbidity. Recently, low dose CT screening of high risk groups allowed for earlier diagnosis of the disease in a significant number of patients [2]. As a result, thoracic surgeons are increasingly faced with the challenge of localization and resection of small lung tumors that are often non-visible and non-palpable. Suzuki et al. [3] reported that frequent conversion to thoracotomy (54%) is needed due to failure to localize nodules (46%). Therefore, there is a need for the development of novel techniques for localization of small, non-visible, non-palpable pulmonary nodules during minimally invasive surgery. One example of a standard procedure for intraoperative localization of small sized nodules is CT-guided micro-coil placement performed prior to video assisted thoracic surgery (VATS). The coil is then visualized under fluoroscopy during surgery and eventually resected together with the pulmonary nodule. However, issues with this technique include pneumothorax which limits the ability of marking a second lesion. Radiation exposure for both the patient and surgical staff associated with intraoperative fluoroscopy is also a disadvantage. The employment of a nano-sized CT/optical imaging agent has the potential to significantly improve low-dose CT-based localization of small pulmonary nodules pre-operatively and the subsequent visualization and localization of the same lesions under near-infrared (NIR) fluorescence thoracoscopy during minimally invasive surgery.

Head and neck (H&N) cancer surgery involves resection tasks in close proximity to critical structures, which can potentially limit surgical performance even for the experienced surgeon. Clinicians must also contend with complex 3D anatomical structures that are subject to variations across the patient population and morphological changes due to disease pathology or prior surgery. The need for precise surgical guidance that accounts for intraoperative anatomical deformation and tissue excision has motivated the development of imaging systems for intraoperative guidance. The development and use of low dose cone-beam CT (CBCT) imaging for surgical guidance has been reported [4, 5]. Extensive investigation in clinical head and neck, otology, orthopedic, lung, and spine surgery has successfully demonstrated the benefit of intraoperative CBCT for improved target localization and avoidance of critical structures. Specifically for H&N surgery, the relevance of CBCT image-guidance has been demonstrated in a variety of preclinical settings [6, 7] and in a prospective clinical trial completed [8].

SUMMARY

Described herein is the development and preclinical characterization of a dual-modality x-ray computed tomography (CT) and near-infrared (NIR) fluorescence liposome-based agent (CF800, FIG. 1) useful for pre-operative CT-based surgical planning and intra-operative optical guidance. The successful clinical translation of such an agent can improve the accuracy of tumor resection in image-guided surgery. For example, described herein is the improvement in imaging performance of CT and CBCT achieved through the administration of the long-circulating CF800 agent with the ability to provide significant pre-, intra- and post-operative contrast enhancement of blood vessels, soft tissue and tumor. Further, more accurate malignant tissue resection is achieved through intraoperative fluorescence visualization of tumor margins and potential lymph node involvement Accordingly, the present application includes a composition comprising an iodinated contrast agent and indocyanine green co-encapsulated inside a liposomal carrier.

The present application also includes a use of a composition of the application for dual modality imaging.

The present application also includes a method for performing dual modality imaging in a subject in need thereof comprising administering an effective amount of a composition of the application to the subject and performing CT and fluorescence imaging, for example NIR-fluorescence imaging, on the subject.

The present application also includes a method for the manufacture of a liposome composition comprising indocyanine green and an iodinated contrast agent, the method comprising:

a) combining one or more neutral lipids, cholesterol and one or more PEGylated lipids with an organic solvent at a temperature of about 40° C. to about 80° C.;
b) combining indocyanine green with a solution comprising the iodinated contrast agent at a temperature of about 20° C. to about 70° C.;
c) mixing the combination from a) with the combination from b) under conditions to obtain multilamellar liposomes; and
d) extruding the liposomes at a pressure of about 50 psi to about 1000 psi.

In an embodiment, the lipid mixture comprises PC, cholesterol and PEGylated-PE, optionally at a molar ratio of about 55:40:5.

In an embodiment the iodinated contrast agent is iohexol.

In an embodiment, the molar ratio of iodinated contrast agent to indocyanine green is about 10,000:1 to about 100:1, optionally about 1000:1.

In another embodiment the liposomal carrier comprises one or more neutral lipids, cholesterol and one or more PEGylated lipids.

In an embodiment, the indocyanine green in the liposome composition retains at least 50% of its original fluorescence for at least 24 hours, optionally, 48 hours, optionally 72 hours, 120 hours, optionally 240 hours.

Other features and advantages of the present application will become apparent from the following detailed description. It should be understood, however, that the scope of the claims should not be limited by the preferred embodiments set forth in the examples, but should be given the broadest interpretation consistent with the description as a whole.

BRIEF DESCRIPTION OF THE DRAWINGS

The present application includes references to appended drawings in which.

DESCRIPTION OF VARIOUS EMBODIMENTS (i) Definitions

Figure 1:
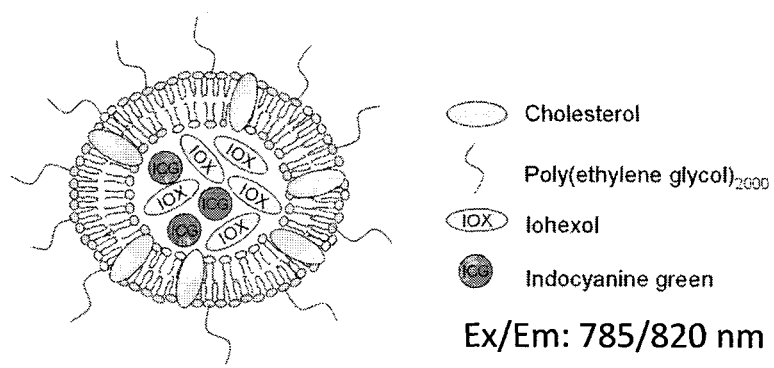
FIG. 1 shows a schematic drawing (not to scale) of a CT/optical liposome system in one embodiment of the present application.

Unless otherwise indicated, the definitions and embodiments described in this and other sections are intended to be applicable to all embodiments and aspects of the application herein described for which they are suitable as would be understood by a person skilled in the art.

As used in this application, the singular forms "a", "an" and "the" include plural references unless the content clearly dictates otherwise. For example, an embodiment including "a solvent" should be understood to present certain aspects with one solvent, or two or more additional solvents.

In embodiments comprising an "additional" or "second" component, such as an additional or second solvent, the second component as used herein is chemically different from the other components or first component. A "third" component is different from the other, first, and second components, and further enumerated or "additional" components are similarly different.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product described.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "PEGylated" as used herein refers to a molecule to which a polyethylene glycol (PEG) polymer chain has been covalently attached. PEGylation is routinely achieved by incubation of a reactive derivative of PEG with the target molecule. The covalent attachment of PEG to a molecule can "mask" the molecule from the host's immune system (reduced immunogenicity and antigenicity), and increase the hydrodynamic size (size in solution) of the molecule which prolongs its circulatory time by reducing renal clearance. PEGylation can also provide water solubility to hydrophobic molecules.

The term "dual modality imaging" as used herein refers to imaging a subject using two different imaging modalities or techniques.

The term "subject" as used herein refers to all members of the animal kingdom, including mammals, for example humans.

The term "co-encapsulated" as used herein means that at least a portion of the specified reagents, i.e. an iodinated contrast agent and indocyanine green, are retained within the liposomal aqueous core found inside the bilayer of the liposome. In an embodiment, the portion of the reagents that is retained within the liposomal aqueous core found inside the bilayer of the liposome is an effective amount of the reagents. In an embodiment, the effective amount of the iodinated contrast agent is an amount effective for CT imaging in the subject. In an embodiment, the effective amount of indocyanine green is an amount effective for fluorescence imaging, in particular near-infrared (NIR) fluorescence imaging, in the subject.

(ii) Compositions of the Application and Methods of Use Thereof

The present application includes a composition comprising an iodinated contrast agent and indocyanine green co-encapsulated inside a liposomal carrier.

In an embodiment the iodinated contrast agent is iohexol. In another embodiment, the iohexol is in an aqueous solution comprising the iohexol. In another embodiment, the aqueous solution comprising iohexol further comprises one or more of therapeutic agents and/or metal chelating agents and the pH is adjusted to between about 6.5 and about 8.0, optionally between about 6.8 and about 7.7.

In an embodiment, the composition is pharmaceutical composition that is suitable for or compatible for administration to or use in human and animal subjects. In an embodiment, the pharmaceutical composition comprises an effective amount of the iodinated contrast agent and indocyanine green. In an embodiment, the effective amount of the iodinated contrast agent is an amount effective for CT imaging in the subject. In an embodiment, the effective amount of indocyanine green is an amount effective for fluorescence imaging, in particular near-infrared (NIR) fluorescence imaging, in the subject. Such amounts are readily determined by a person skilled in the art and are independent of each other. In a further embodiment, the indocyanine green is sensitive to light and therefore is protected from exposure to light.

In an embodiment, the molar ratio of iodinated contrast agent to indocyanine green is about 10,000:1 to about 10:1, optionally about 1000:1. In an embodiment, the weight ratio of iodine to indocyanine green is about 10,000:1 to about 10:1, optionally about 500:1.

In another embodiment the liposomal carrier comprises one or more lipids, cholesterol and, optionally, one or more PEGylated lipids. In an embodiment, the one or more lipids is a neutral lipid such as a phosphatidylcholine (PC), for example dipalmitoylphosphatidylcholine (DPPC). In a further embodiment, the one or more PEGylated lipids is a PEGylated phosphatidylethanolamine (PEG-PE), such as PEGylated Distearoylphosphoethanolamine (PEG-DSPE). In an embodiment, the liposomal carrier comprises (in molar %) about 40% to about 60% of the lipid, about 20% to about 40% of the cholesterol and about 0 to about 5% of the PEGylated lipid. In an embodiment, the liposomal carrier comprises the one or more lipids, cholesterol and one or more PEGylated lipids at a molar percent ratio of about 55:40:5.

In an embodiment, the indocyanine green in the liposome composition retains at least about 50%, about 70%, about 75% or about 80% of its original fluorescence for at least about 24 hours, about 48 hours, about 72 hours, about 120 hours, or about 240 hours.

In an embodiment, the compositions of the application are formulated for administration by injection. For example, the compositions are formulated for intravenous, intraperitoneal, subcutaneous, intramuscular, intrapulmonary or intrathecal modes of injection. In an embodiment, the mode of injection is intravenous (i.v). In another embodiment, the compositions of the application are formulated for administration by inhalation, such as by spray or aerosol.

In an embodiment, the compositions are lyophilized, for example, and rehydrated and resuspended in an aqueous solution prior to use.

The present application also includes a kit comprising a composition of the application and instructions for use, for example for imaging, in particular dual modality imaging. In an embodiment, the kit comprises a composition of the application that has been lyophilized and, optionally, an aqueous solution and/or buffer and instructions for reconstitution of a solution prior to use in imaging. In another embodiment, the kit comprises of two aqueous solutions to be mixed prior to administration. For example, the kit may comprise the liposomal composition of the present application and two different concentrations. In an embodiment, the kit further comprises other components that are used during imaging as would be known to those skilled in the art.

The present application also includes a use of a composition of the application for imaging using one or more imaging modality or technique. In an embodiment, the compositions are used for dual modality imaging.

The present application also includes a method for imaging subject in need thereof comprising administering an effective amount of a composition of the application to the subject and imaging on the subject. In an embodiment, the subject is imaged using one or more imaging modalities or techniques. In another embodiment, the subject is imaged using two or more imaging modalities or techniques. In an embodiment, the imaging modalities are selected from one or more of x-ray fluoroscopy, CT, cone-beam CT, dual-energy CT, optical imaging, fluorescence imaging and near-infrared fluorescence imaging. The present applications also includes a method for performing dual modality imaging in a subject in need thereof comprising administering an effective amount of a composition of the application to the subject and performing CT and fluorescence imaging, for example NIR-fluorescence imaging, on the subject.

In an embodiment, the subject has cancer. In an embodiment, the cancer is breast cancer, ovarian cancer, lung cancer, oral cancer, head and neck cancer, prostate cancer, liver cancer or any type of cancer in which the a tumor is imaged using the compositions of the application.

In an embodiment, imaging of vascular structures is performed using one or more modalities including x-ray fluoroscopy, CT, cone-beam CT, dual-energy CT, optical imaging, fluorescence imaging and near-infrared fluorescence imaging following administration of a composition of the application to a subject.

In another embodiment, the subject is and/or will be undergoing surgery. In an embodiment the surgery is a video assisted thoracic surgery (VATS), a surgery using low dose cone-beam CT imaging (CBCT), a surgery using x-ray fluoroscopy guidance, a surgery using CT image-guidance, a surgery using dual-energy CT image-guidance, a surgery using optical image-guidance or any other surgical procedure where the compositions of the application modifies imaging signal and/or contrast.

(iii) Methods for Manufacture

The present application also includes a method for the manufacture of a liposome composition comprising indocyanine green and an iodinated contrast agent, the method comprising:

a) combining one or more neutral lipids, cholesterol and one or more PEGylated lipids with an organic solvent at a temperature of about 40° C. to about 80° C.;

b) combining indocyanine green with a solution comprising the iodinated contrast agent at a temperature of about 20° C. to about 70° C.;

c) mixing the combination from a) with the combination from b) to under conditions to obtain multilamellar liposomes; and d) extruding the liposomes at a pressure of about 50 psi to about 1000 psi.

In an embodiment, the organic solvent in a) is a $C_{1-4}$ alcohol such as ethanol or methanol or a chlorinated solvent, such as chloroform. In a further embodiment, the organic solvent is ethanol.

In an embodiment, the temperature in a) is about 60° C. to about 80° C. In an embodiment, the temperature in a) is about 72° C.

In an embodiment, the temperature in b) is about 30° C. to about 70° C. In an embodiment, the temperature in b) is about 50° C.

In an embodiment, the mixing of the combination from a) with the combination from b) to obtain multilamellar liposomes is performed for at least about four hours with periodic mixing.

In an embodiment, the liposomes are extruded in d) at a pressure of about 100 psi to about 500 psi, or about 100 psi to about 400 psi.

In an embodiment, the iodinated contrast agent is iohexol. In another embodiment, the iohexol is in an aqueous solution comprising the iohexol. In another embodiment, the aqueous solution comprising iohexol further comprises one or more of therapeutic agents and metal chelating agents and the pH is adjusted to between about 6.5 and about 8.0, optionally between about 6.8 and about 7.7.

In an embodiment, the molar ratio of iodinated contrast agent to indocyanine green is about 10,000:1 to about 100:1, optionally about 1000:1. In an embodiment, the weight ratio of iodine to indocyanine green is about 10,000:1 to about 10:1, optionally about 500:1.

In another embodiment the liposomal carrier comprises one or more lipids, cholesterol and, optionally, one or more PEGylated lipids. In an embodiment, the one or more lipids is a neutral lipid such as a phosphatidylcholine (PC), for example dipalmitoylphosphatidylcholine (DPPC). In a further embodiment, the one or more PEGylated lipids is a PEGylated phosphatidylethanolamine (PEG-PE), such as PEGylated Distearoylphosphoethanolamine (PEG-DSPE). In an embodiment, the liposomal carrier comprises (in molar %) about 40% to about 60% of the lipid, about 20% to about 40% of the cholesterol and about 0 to about 5% of the PEGylated lipid. In an embodiment, the liposomal carrier comprises the one or more lipids, cholesterol and one or more PEGylated lipids at a molar percent ratio of about 55:40:5.

In an embodiment, the method further comprises formulating the liposome compositions of the present application into a pharmaceutical formulation. In an embodiment, the pharmaceutical composition comprises an effective amount of the iodinated contrast agent and indocyanine green. In an embodiment, the effective amount of the iodinated contrast agent is an amount effective for CT imaging in the subject. In an embodiment, the effective amount of indocyanine green is an amount effective for fluorescence imaging, in particular near-infrared (NIR) fluorescence imaging, in the subject. Such amounts are readily determined by a person skilled in the art and are independent of each other. In a further embodiment, indocyanine green is sensitive to light and therefore is protected from exposure to light.

In an embodiment, the pharmaceutical formulations are for administration by injection and the method comprises appropriate steps to prepare such formulations as described above. In a further embodiment, the pharmaceutical formulations are for administration by inhalation, such as spray and aerosol formulations, and the method comprises appropriate steps to prepare such formulations as described above A method for the manufacture of a liposome formulation comprising indocyanine green and iodinated contrast agent, the method comprising:
dissolving a mixture consisting of one or more lipids, cholesterol and one or more PEGylated lipids in an organic solvent, optionally ethanol, at a temperature between 50-100° C., optionally 72° C.;
pre-dissolving indocyanine green in the iodinated contrast agent solution at a temperature between 30-70° C., optionally 50° C.;
mixing or hydrating the mixture from step a) with the mixture from step b), optionally for at least four hours with vortexing to obtain multilamellar vesicles; and
extruding the vesicles at a pressure between 50 psi and 1000 psi, optionally, 100 to 500 psi, optionally 100 to 400 psi.

The method of as defined above, wherein the lipid mixture comprises DPPC, cholesterol and $PEG_{2000}DSPE$, optionally at a molar ratio of 55:40:5.

The method of as defined above, wherein the iodinated contrast agent is iohexol, optionally Omnipaque®.

The method of as defined above, wherein the indocyanine green in solution retains at least 50% of its original fluorescence for at least 24 hours, optionally, 48 hours, optionally 72 hours, 120 hours, optionally 240 hours.

The method of as defined above, wherein the indocyanine green in solution retains at least 70%, optionally 75%, optionally 80%.

EXAMPLES

Materials

The components of liposomes: 1,2-Dipalmitoyl-sn-Glycero-3-Phosphocholine (DPPC, M.W. 734), Cholesterol (CH, M.W. 387) and 1,2-Distearoyl-sn-Glycero-3-Phosphoethanolamine-N-[Poly(ethylene glycol)2000] ($PEG_{2000}DSPE$, M.W. 2774) were purchased from Northern Lipids Inc. (Vancouver, British Columbia, Canada). The CT contrast agent, Omnipaque® was obtained from GE Healthcare. Omnipaque® (350 mg/mL of iodine) contains iohexol (M.W. 821.14), an iodinated, water-soluble, non-ionic monomeric contrast medium. Each milliliter of Omnipaque® iohexol solution contains 1.21 mg tromethamine and 0.1 mg edetate calcium disodium with the pH adjusted between 6.8 and 7.7 with hydrochloric acid or sodium hydroxide. The fluorescence agent indocyanine green (ICG or IR-125) was purchased from Acros Organics.

Preparation of Liposome Formulation

Lipid mixtures (200 mmol/L) of DPPC, cholesterol and $PEG_{2000}DSPE$ in 55:40:5 percent mole ratios were dissolved in ethanol at 72° C. All steps involving ICG will be conducted in a low light environment (i.e. using aluminum wrapping). The lipid-ethanol solution was then hydrated (for at least 4 hours with periodical mixing) at 72° C. with ICG pre-dissolved in Omnipaque® (at 50° C. for 20 minutes). The initial ethanol content was $10\%_{vol}$. The resulting multilamellar vesicles were then either immediately extruded or kept at room temperature and extruded the next day (with pre-heating at 72° C. for 2 hours) with a Lipex™ Extruder (Northern Lipids Inc., Vancouver, British Columbia, Canada) at 72° C. Specifically, the samples were first extruded[9, 10] 5 times with two stacked polycarbonate membranes of 0.2 μm pore size (Nucleopore® Track-Etch Membrane, Whatman Inc., Clifton, N.J., USA) and subsequently 5 times with two stacked polycarbonate membranes of 0.08 μm pore size. The nitrogen pressure used throughout the extrusion was between 100-400 psi. The purification of the resulting unilamellar liposome sample was performed using a Sephadex G-25 (GE Healthcare) column loaded on a 1.5×120 cm Kontes® Flex-column (VWR). The Sephadex G-25 suspension was prepared using the HEPES buffer solution (HBS, pH 7.4) at a 1:10 volume ratio. 500 mL of HBS was used to wash the column following packing. Up to 5 mL of the liposome sample can be loaded at a time into one column for purification, and the sample is eluted using HBS buffer. The liposome fraction can be monitored visually by the ICG color and the turbidity of the elution drop. Following collection of the eluted liposome fractions, a tangential flow apparatus is used to re-concentrate the solution as dilution in HBS has occurred during the column purification process. The final solution is then tested for iohexol and ICG encapsulation (UV absorbance at 245 nm and 785 nm respectively), size, zeta potential and lipid content (ultra-performance liquid chromatography with an evaporative light scattering detector).

The liposome bilayer was composed of 1,2-dipalmitoyl-sn-glycero-3-phosphocholine (DPPC, CordenPharma, Liestal, Switzerland), cholesterol (Northern Lipids Inc., Vancouver, BC, Canada) and 1,2-distearoyl-sn-glycero-3-phosphoethanolamine-N-[poly(ethylene glycol)2000] ($PEG_{2000}DSPE$, CordenPharma, Liestal, Switzerland) in a percent mole ratio of 55:40:5. The liposome preparation procedure is modified from a previously published protocol [12,16]. Specifically, the lipid mixture was first dissolved in ethanol and then hydrated for 4 h at 70° C. in a solution of 300 μg of ICG (IR-125, Acros Organics, Geel, Belgium) dissolved in Omnipaque350® (GE Healthcare, Milwaukee, Wis.). The resulting liposome solution was extruded at pressures between 100-400 psi using the LIPEX™ Extruder (Northern Lipids Inc., Vancouver, Canada). Purification was performed using a Sephadex G-25 column. The final liposome sample was kept at room temperature protected from light until use.

The size of the liposome samples was measured using dynamic light scattering (DLS) (90Plus, Brookhaven, Holtsville, N.Y.). The iodine and ICG concentrations were determined using an absorbance assay at a wavelength of 245 nm for iodine and 785 nm for ICG (Cary 50 UV/VIS Spectrophotometer, Varian Inc., Palo Alto, Calif.). The lipid components of the liposome sample was analyzed using ultra performance liquid chromatography (UPLC, ACQUITY, Waters, Milford, Mass.) equipped with an evaporative light scattering detector (ELSD). The in vitro fluorescence measurements were performed using a 2D fluorescence imager (excitation/emission: 735/820 nm, CRI Maestro, Perkin Elmer, Waltham, Mass.).

Evaluation of Imaging Performance in Animal Models

All preclinical investigations were approved by the University Health Network Animal Care Committee and adhered to the ethical guidelines of the Canadian Council on Animal Care. Two metastatic models of human cancer in SCID mice were employed: SKOV-3/Luc ovarian adenocarcinoma inoculated intraperitoneally and LM2-4H2N (a Her-2 positive and metastatic variant of MDA-MB-231) inoculated into the right inguinal mammary fat pad. Both cell lines used express the firefly luciferase reporter gene, allowing for non-invasive monitoring of tumor growth and metastasis using bioluminescence imaging (BLI, IVIS, Perkin Elmer). Following confirmation of successful metastasis formation by BLI, each mouse was i.v. injected with CF800 (0.6 mg/g of iodine and 1 µg/g of ICG co-encapsulated in liposomes). CT imaging (80 kVp, 0.5 mA, GE Locus Ultra) was performed pre-injection and at 4, 24 and 48 h post-injection. At 48 h post-injection, animals were sacrificed and their peritoneal cavities were exposed for post-mortem 2D NIR fluorescence (Maestro, Perkin Elmer) and CT imaging. This was done to assess the target-to-background signal emitted by malignant nodules and to evaluate the co-localization of the CT and fluorescence signals. Finally, critical healthy organs (heart, liver, spleen and kidneys) and metastatic tumor nodules were excised and imaged using both modalities.

Two disseminated models of human cancer in female SCID mice were employed: 1) SKOV-3/Luc ovarian adenocarcinoma (purchased from Cell Biolabs Inc., San Diego, Calif.) inoculated intraperitoneally ($3 \times 10^6$ cells in 100 µL), and 2) LM2-4H2N/Luc (a metastatic variant of the breast cancer cell line MDA-MB-231 [17]) injected into the right lower mammary fat pad ($4 \times 10^6$ cells in 50 µL). Bioluminescence imaging (IVIS Imaging System, Perkin Elmer, Waltham, Mass.) at 10 min post i.p. injection of 150 mg/kg D-luciferin was used to monitor tumor growth and metastasis formation in all mice. Rabbit models of VX-2 buccal mucosa and lung cancer were also employed in this study. For the buccal mucosa tumor model, 300⍳ of a VX-2 carcinoma cell suspension ($5 \times 10^6$ cells/mL) obtained from propagation rabbits [18] was injected into the buccinator muscle of New Zealand White rabbits (Charles River, Wilmington, Mass.). Tumors were formed at the site of VX-2 cell injection and all rabbits presented with at least one cervical lymph node metastasis at two weeks post inoculation. The VX-2 rabbit lung tumor model was established according to previously reported methods [19].

CF800 is further tested in a rabbit model of VX-2 buccal mucosa carcinoma implanted in the cheek. Approximately 20 mL of the liposome solution was administered as a slow i.v. bolus (0.3 g/kg of iohexol and 0.8 mg/kg of ICG co-encapsulated in liposomes, mean diameter of ~90 nm). CT imaging was performed pre and at 5-30 min and 1, 2, 4, and 8 days post-injection. NIR fluorescence imaging using the SPY system (NOVADAQ) was conducted during either survival and non-survival surgery for tumor and lymph node resection on either day 4 or 8 post-liposome administration.

Each mouse (20-25 g) received 200⍳ of the liposome formulation i.v. (0.58±0.05 mg/g of iodine and 1.2±0.3 µg/g of ICG, diameter=86±4 nm) and each rabbit (2.6-3.0 kg) received 20 mL of the liposome formulation i.v. (0.39±0.02 g/kg of iodine and 1.0±0.3 mg/kg of ICG, diameter=90±2 nm). CT imaging (Locus Ultra, GE Healthcare, Milwaukee, Wis.) was performed pre and post liposome administration (80 kVp, 50 mA). It is estimated that the total whole body dose per mouse per scan is less than 10 cGy [20], this is ~1% of the LD50/30 (radiation dose lethal for 50% of mice within 30 days post-exposure) reported for mice [21]. For the mouse study, at 48 h p.i., animals were sacrificed and their peritoneal cavities were exposed for post-mortem CT and 2D NIR fluorescence imaging to evaluate the co-localization of the CT and fluorescence signals. For the rabbit study, image-guided surgical removal of the primary tumor and involved lymph nodes was performed at 4-7 days post-liposome administration. Real-time fluorescence imaging (overlaid with white light) of the surgical site containing the tumor and malignant lymph nodes was performed using the PINPOINT® system (808±5 nm, Novadaq, Mississauga, Canada).

All CT-based image analysis was performed using Microview (GE Healthcare, Milwaukee, Wis., USA) and custom in-house code written using MATLAB (MathWorks®, Natick, Mass.). The tumor volumes were contoured using a semi-automated threshold based method [12] and the blood volume-of-interest (VOI) were drawn manually on the right carotid artery. The mean and standard deviation of the voxel signal distribution within each VOI was calculated. All NIR fluorescence image analysis was performed using ImageJ (National Institute of Health, Bethesda, Md.) by manually placing regions-of-interest (ROI) on selected structures of interest and background and measuring the mean and standard deviation of the signal level over multiple image frames.

Post tumor and organ excision, tissue samples were fixed in formalin, embedded in paraffin blocks, cut and stained with hematoxylin and eosin and Ki-67. An experienced pathologist (Dr. Stefano Serra) evaluated all histo-pathology slides for disease identification and confirmation.

Results:

The CF800 liposomes (FIG. 1) co-encapsulates a commercially available CT contrast agent iohexol and a clinically approved NIR optical dye indocyanine green (ICG) at a mole ratio of 1000:1 (iohexol to ICG) and a weight ratio of 500:1 (iodine to ICG). The difference in concentration for the two encapsulated imaging agents was set to compensate for the difference in detection sensitivity between CT and fluorescence imaging. We also successfully showed our ability to reproducibly fabricate the dual-modality liposomes with consistent particle size, lipid and imaging molecule concentrations (FIG. 1).

Figure 2:
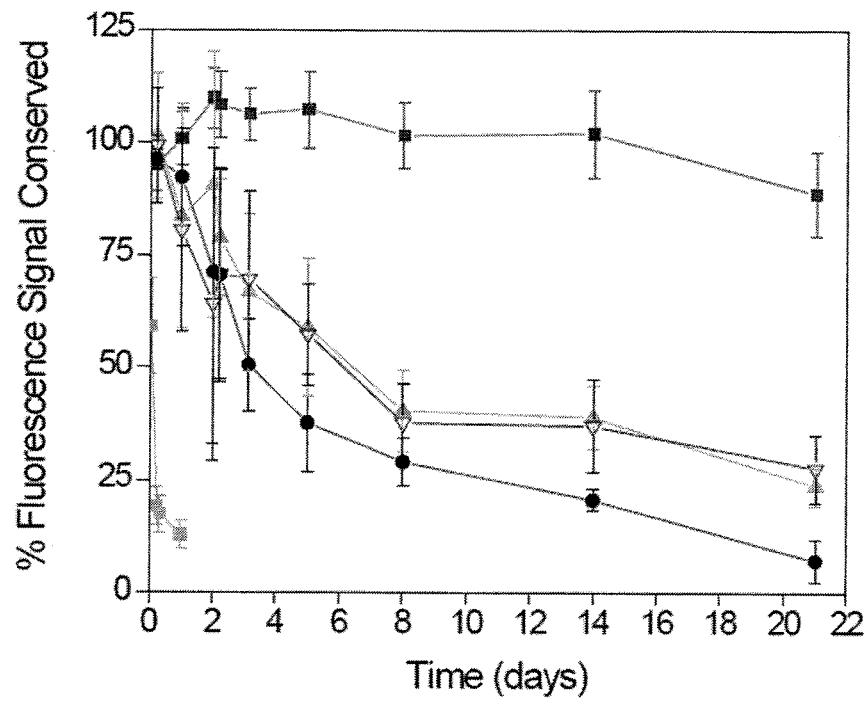
FIG. 2 shows: a) Demonstration of the significant improvement in ICG photostability when co-encapsulated within the CF800 liposomes in an exemplary embodiment of the present application. In vitro investigation of the photostability (following storage at room temperature) of ICG when co-encapsulated with iohexol inside liposomes (squares), when dissolved in water (grey solid triangles), in a 10/90 EtOH/water solution (black circles), in a 5/95 Omnipaque®/water solution (open black triangles) and in Omnipaque® (grey squares) in an exemplary embodiment of the present application. Each data point represents the mean±standard deviation measured either from duplicate samples from 3 separate production batches (ICG in liposomes) or 7 samples of varying ICG concentrations (ranging from 0.5-2.5 µg/mL) for all other ICG solutions. b) Vascular circulation life-time of CF800 in an exemplary embodiment of the present application. Vascular circulation half-lives ($t_{1/2}$) of CF800 in healthy SCID mice (far right, n=9) and SCID mice bearing the metastatic breast cancer xenograft LM2-4H2N (far left, n=13) and the disseminated intraperitoneal SKOV-3 ovarian xenograft model (middle, n=13). The $t_{1/2}$ values are calculated by fitting a one-compartmental pharmacokinetics model using blood iodine levels measured on the same animals over a 48 hour period using CT.
Figure 2:
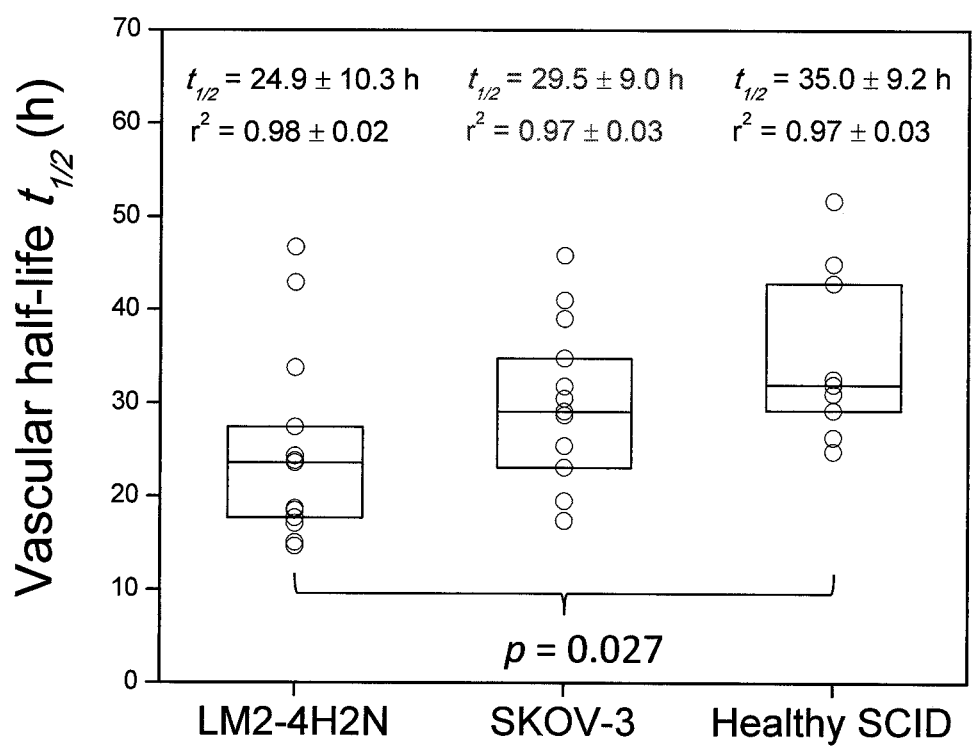

In vitro photostability tests demonstrated that liposomal encapsulation protects ICG from photodegradation, even after repeated excitation. After 3 days of storage at room temperature, following 6 imaging sessions with high-power light exposure, and at a 100-fold dilution in water and a 1:10 ethanol/water mixture, CF800 (n=4) retained 78±8% and 92±11% of its original fluorescence signal, respectively. Free ICG diluted in water, a 1:10 ethanol/water mixture and a 0.5:10 iohexol/water mixture yielded only 8±2%, 3±1%, 7±2% of its original fluorescence, respectively. FIG. 2a shows the results of a separate photostability test conducted up to 21 days showing the high degree of stability of the iohexol and ICG co-encapsulating liposome system compared to ICG diluted in different solutions. The photostability of the encapsulated ICG was investigated by incubating the liposome samples and the free ICG solutions (at 7 physiologically relevant concentrations ranging from 0.5 to 2.5 µg/mL) at room temperature over a 21-day period. It was demonstrated that liposomal co-encapsulation with iohexol significantly extends the photostability of ICG in solution.

The in vivo pharmacokinetics of CF800 was further assessed by imaging the iohexol component in liposomes using high resolution microCT in healthy and tumor-bearing female SCID mice. This CT-based in vivo iodine quantification method was previously validated and published [11, 12]. Each mouse was CT imaged before, and at 15-30 min, 4-6 h, 24 h and 48 h post liposome injection. All pharmacokinetics profiles for all mice investigated (9 healthy SCID mice, 13 SCID mice bearing peritoneally disseminated SKOV-3 ovarian cancer and 13 SCID mice bearing metastatic LM2-4H2N breast cancer) fit a one-compartment model with a mean $R^2$ of 0.98±0.03 across the pharmacokinetics profiles generated from the 37 mice (FIG. 2b). Although the vascular half-life of the CF800 liposomes was seemingly shorter in both sets of tumor-bearing mice compared to healthy mice, this difference was only statistically significant between the LM2-4H2N mice and healthy SCID mice (P<0.05).

In vivo in the two mouse models of cancer, all 13 animals administered with CF800 displayed significantly higher CT attenuation and NIR fluorescence signal in the tumor lesions compared to background (FIG. 3a). The high spatial resolution of CT imaging allows for assessment of the heterogeneous distribution of liposomes inside tumors.

Figure 3:
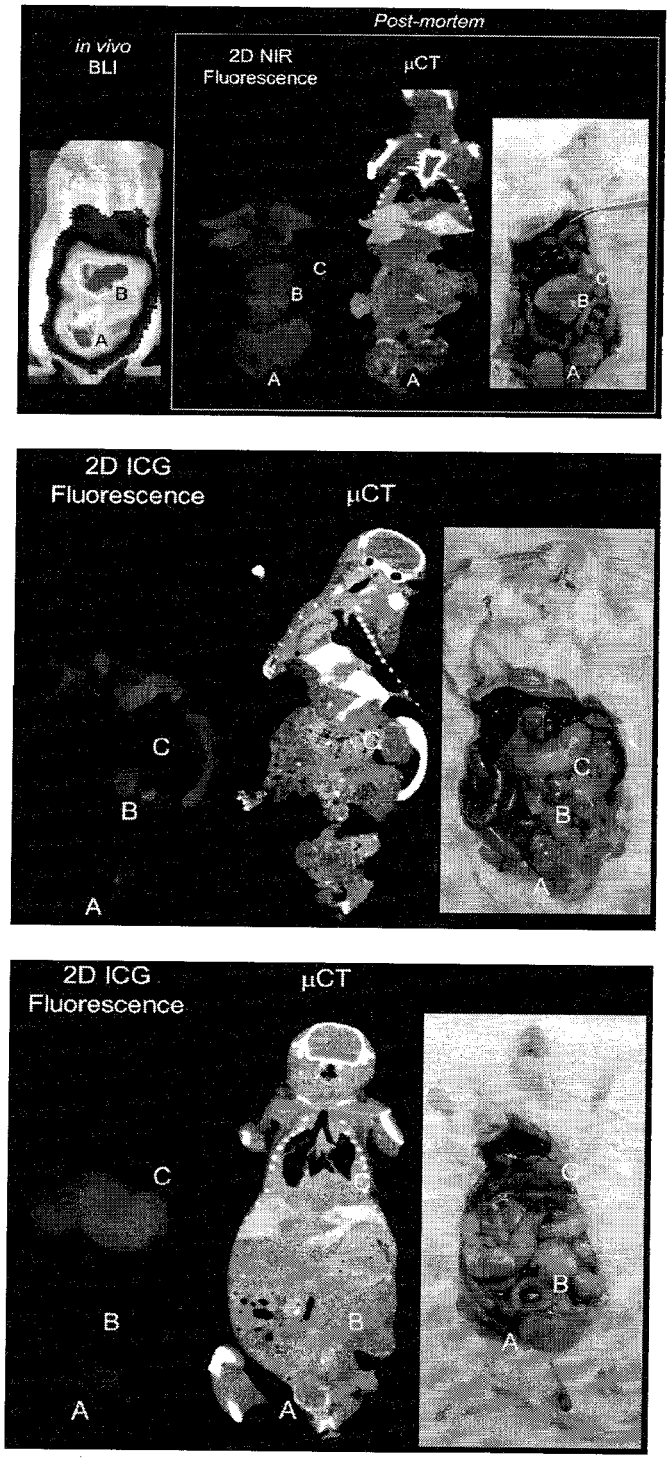
FIG. 3 shows a) Three mice bearing multiple intraperitoneal SKOV-3 tumor nodules imaged at 48 h post-liposome administration in an exemplary embodiment of the present application. Note that the BLI and NIR fluorescence are 2D planar acquisitions, while the CT image shown is a 153 µm 2D slice from a 3D data set. The high signal seen in the liver and spleen is because liposomes routinely accumulate in these organs of the mononuclear phagocytic system. b, c) Pre- and intraoperative imaging using CF800 in mice in exemplary embodiments of the present application. Demonstration of the performance of CF800 in providing CT and NIR fluorescence imaging-based localization and visualization of disseminated and metastatic cancer nodules throughout the peritoneal cavity (T1, T2) and adjacent to the spleen (T3) and liver (T4) in two representative mice (B,C). d) Ex vivo image-based illustration of high and low fluorescence in normal and tumor-bearing organs in three representative mice in exemplary embodiments of the present application. e) Ex vivo image-based illustration of high and low fluorescence metastatic lung nodules, intraperitoneal tumor lesions (A,B) and metastatic lesions excised from the left and right upper mammary fat pads (C,D) in exemplary embodiments of the present application. f) Ex vivo assessment of the mean fluorescence signal measures from the heart, liver, kidney, spleen, lung, tumor and muscle in 8 tumor-bearing (top graph) and 8 healthy SCID mice (bottom graph) in exemplary embodiments of the present application.
Figure 3:
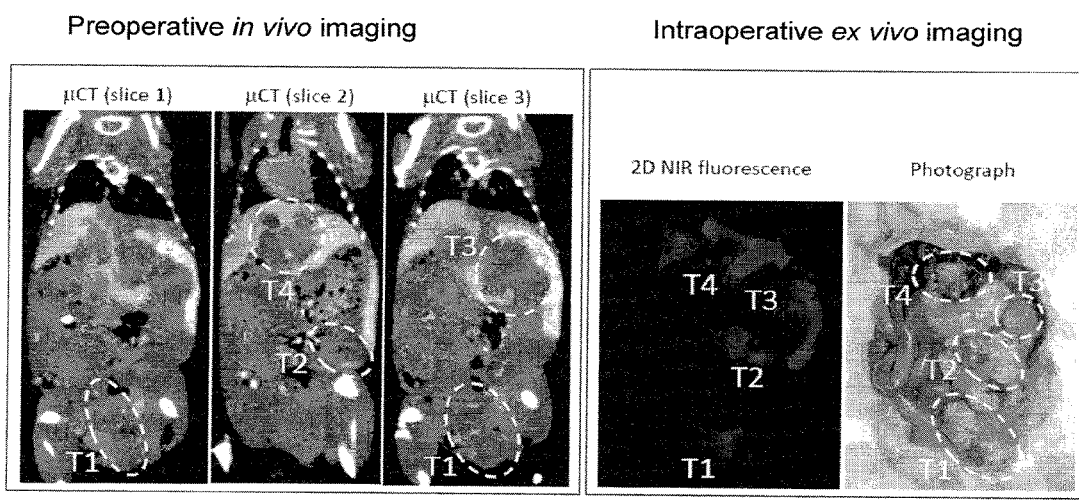
Figure 3:
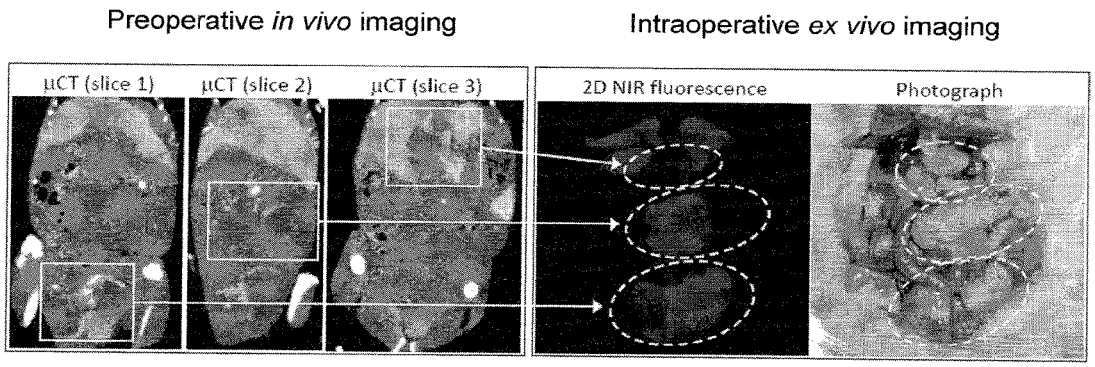
Figure 3:
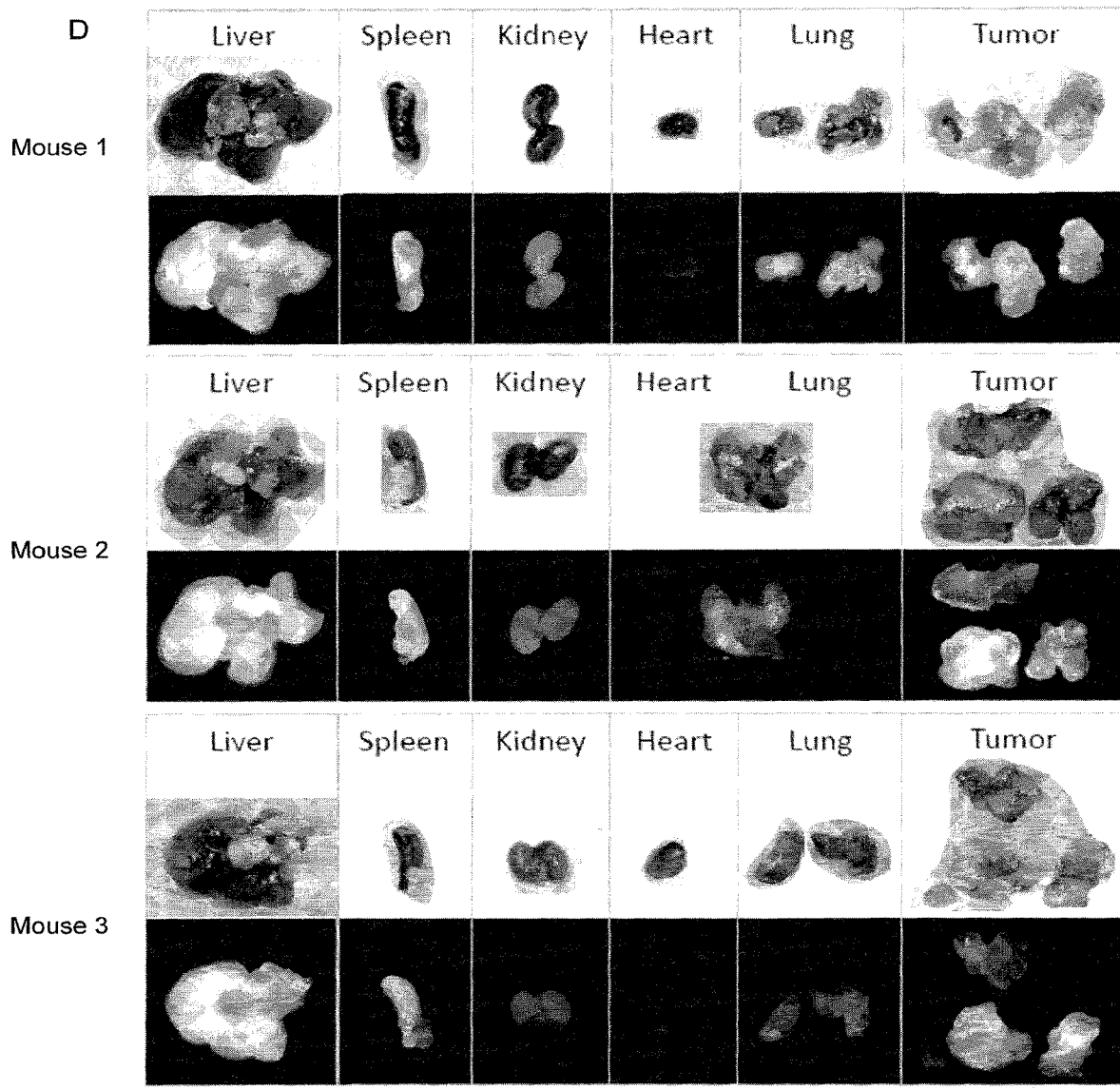
Figure 3:
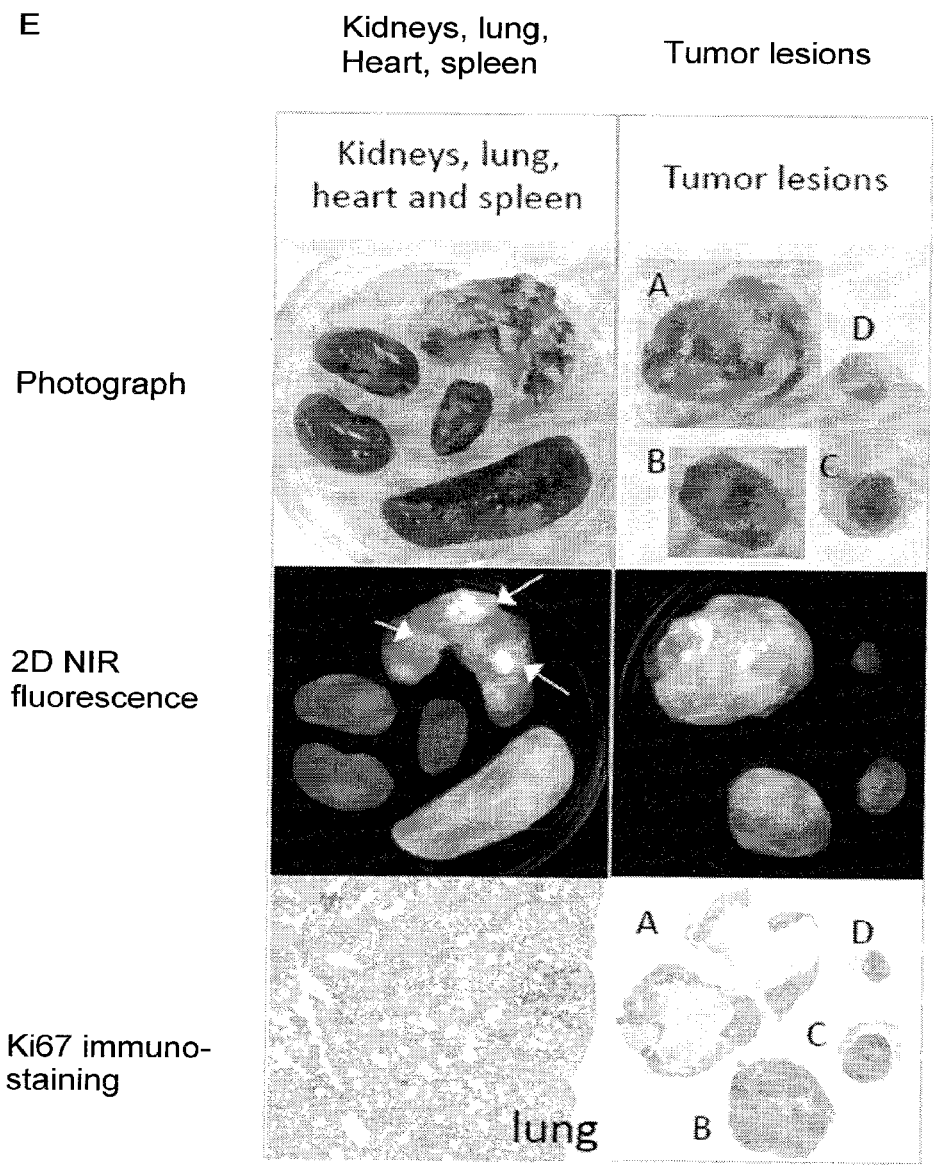
Figure 3:
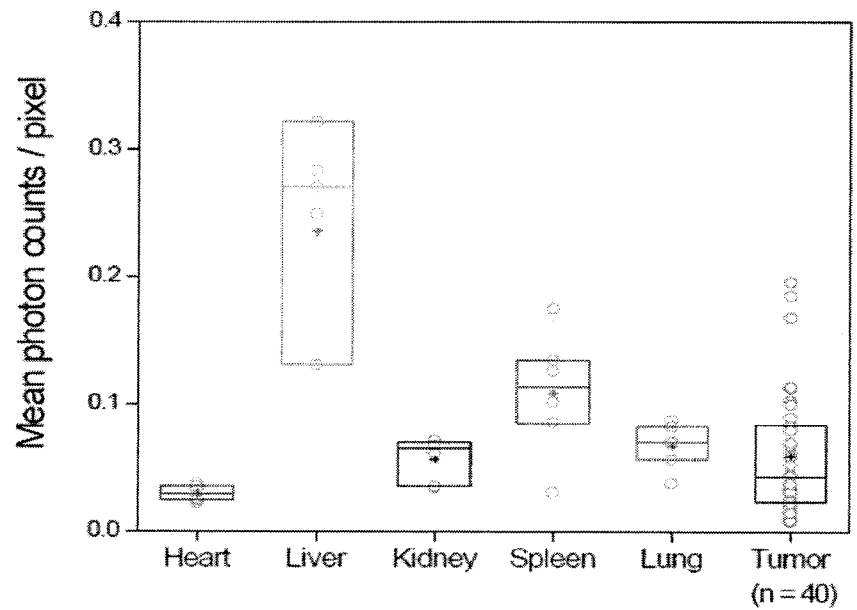
Figure 3:
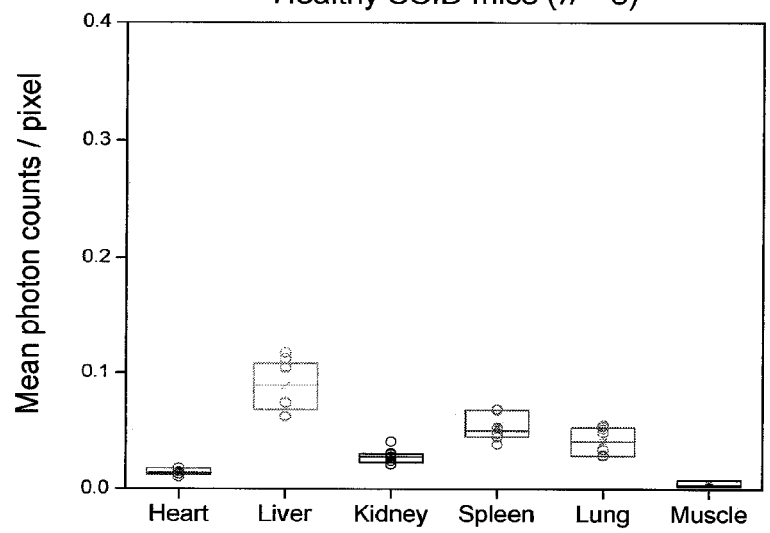
Figure 8:
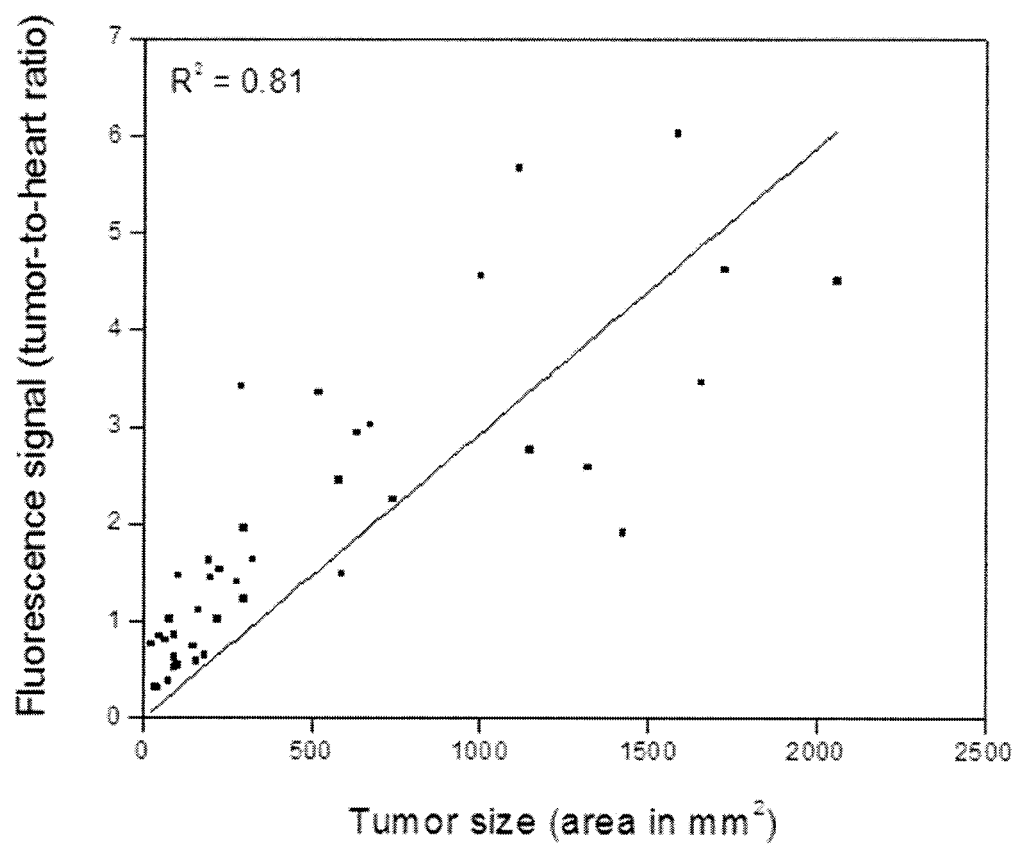
FIG. 8 shows fluorescence signal to tumor size correlation in an exemplary embodiment of the present application. Tumor size is expressed as area in mm² due to the 2D nature of the fluorescence image acquisition. Positive linear correlation ($R^2=0.81$) between normalized liposome accumulation at tumor site and tumor size. Data obtained from 8 mice (5 bearing SKOV-3 ovarian tumor and 3 bearing the LM-24H2N metastatic breast tumor) and 40 disseminated tumor nodules.

Two mouse models of disseminated human cancer were employed (SKOV-3 and LM2-4H2N xenografts) to determine the imaging performance (i.e. nodule identification and localization) of CF800. These models allowed for comprehensive assessment of the tumor visualization capability of CF800 in malignant nodules of varying size, growth condition and background tissue signal (FIG. 3). Specifically, CT imaging was performed at 48 h post-liposome administration and NIR fluorescence images were acquired 1) right after the animals were sacrificed and their tumor bearing areas exposed (i.e. abdomen—FIGS. 3b and c, right panel), and 2) after the tumor nodules and organs of interest were excised (FIGS. 3d and e). Preoperative CT imaging allowed for non-invasive identification of the disseminated tumor nodules with an isotropic voxel size of 154 μm and the CT data was used post-mortem to guide the exposure of deep seated tumor nodules which could not be immediately visualized using NIR fluorescence due to limited light penetration in tissue. Once the abdominal tumor nodules were exposed, NIR fluorescence imaging demonstrated that they could all be visualized as they provided sufficient visual contrast between tumor and background structures. After excision, the different tumor nodules and organs invaded by tumor cells (i.e. liver, spleen and lung) showed higher fluorescence signal variation when compared to the same organs and tissues in healthy animals (FIG. 3f). The heart was used as an organ of reference for fluorescence signal normalization as it was always disease free and showed very little animal-to-animal variability. All organs and tissues investigated (liver, kidney, spleen, lung, tumor and muscle) with the exception of muscle measured higher fluorescence signal than the heart (muscle-to-heart signal ratio=0.5±0.2). As expected, CF800 showed highest accumulation in the liver and the spleen with mean organ-to-heart fluorescence signal ratios of 8.0±4.2 and 3.6±1.6, respectively, a pattern typical of colloidal systems of its size and surface characteristics. Although the mean tumor-to-heart signal ratio is 1.9±1.5 across 40 tumor nodules excised from 8 different animals, the nodule with the highest liposome uptake measured a tumor-to-heart signal ratio of 6.0, while the nodule with the least liposome uptake had a tumor-to-heart signal ratio of 0.3. Overall, there is a positive correlation between the tumor-to-heart mean fluorescence signal ratio and tumor size ($R^2$=0.81, FIG. 8).

Figure 4:
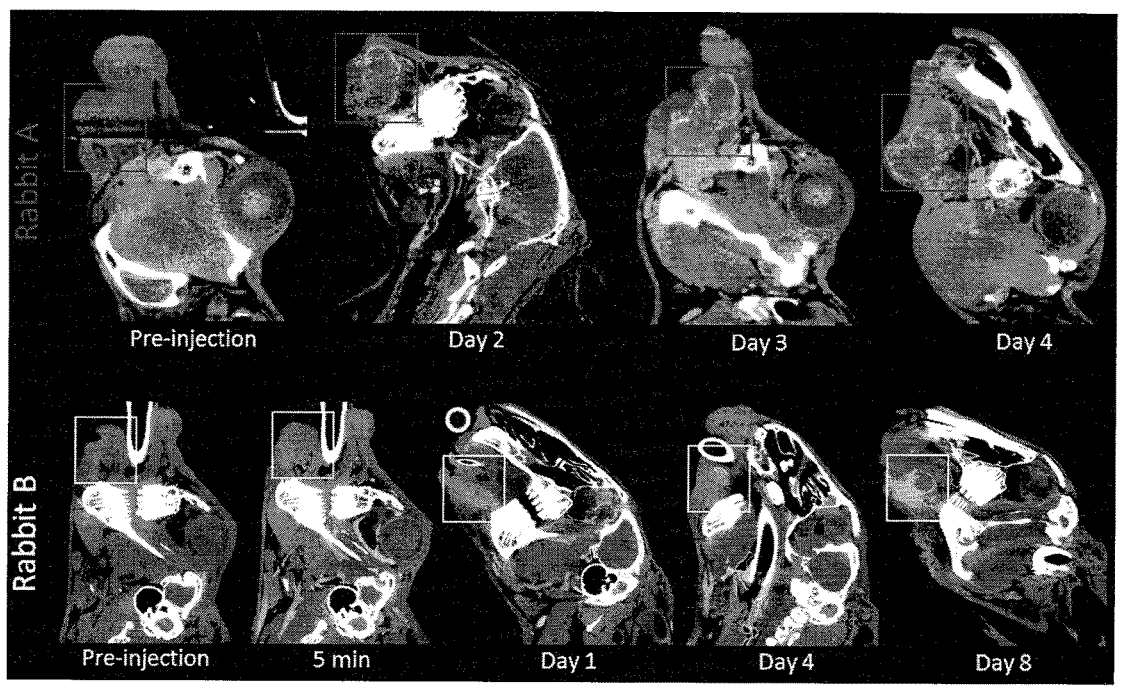
FIG. 4 shows a) CT visualization of the primary tumor site pre-operatively in the VX-2 rabbit buccal mucosa model over an 8-day period in two distinct animals. Imaging performance in rabbit models of cancer. b) Feasibility demonstration of the use of CF800 for preoperative CT and intraoperative NIR fluorescence imaging of the primary tumor (preoperative CT imaging (top panel) and intraoperative NIR fluorescence imaging (bottom panel)) in an exemplary embodiment of the present application.
Figure 4:
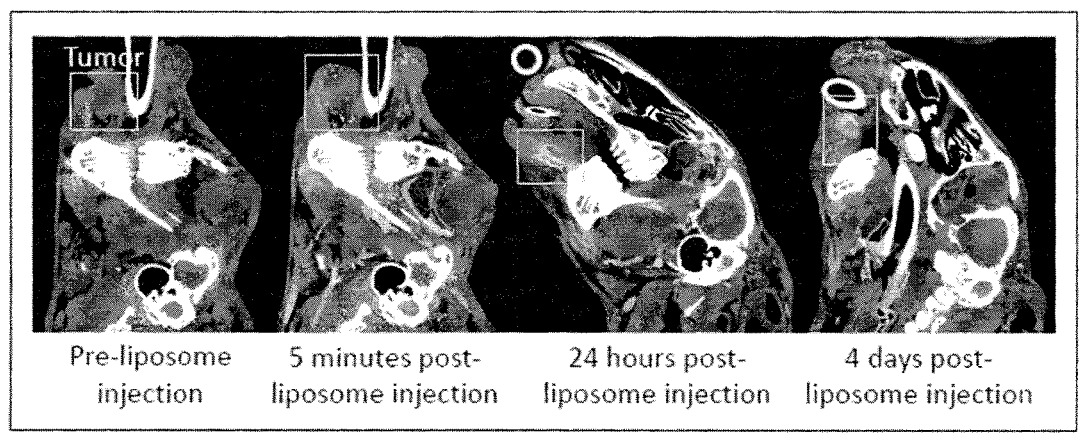
Figure 4:
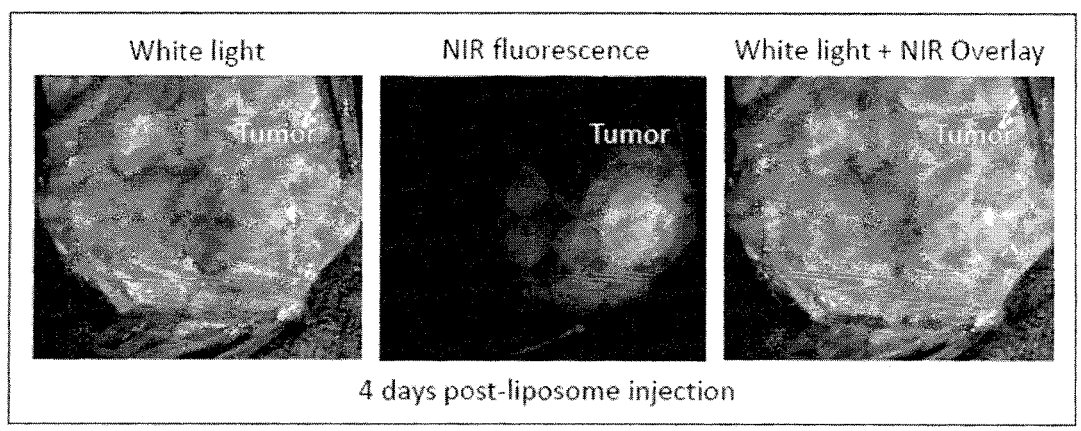
Figure 5:
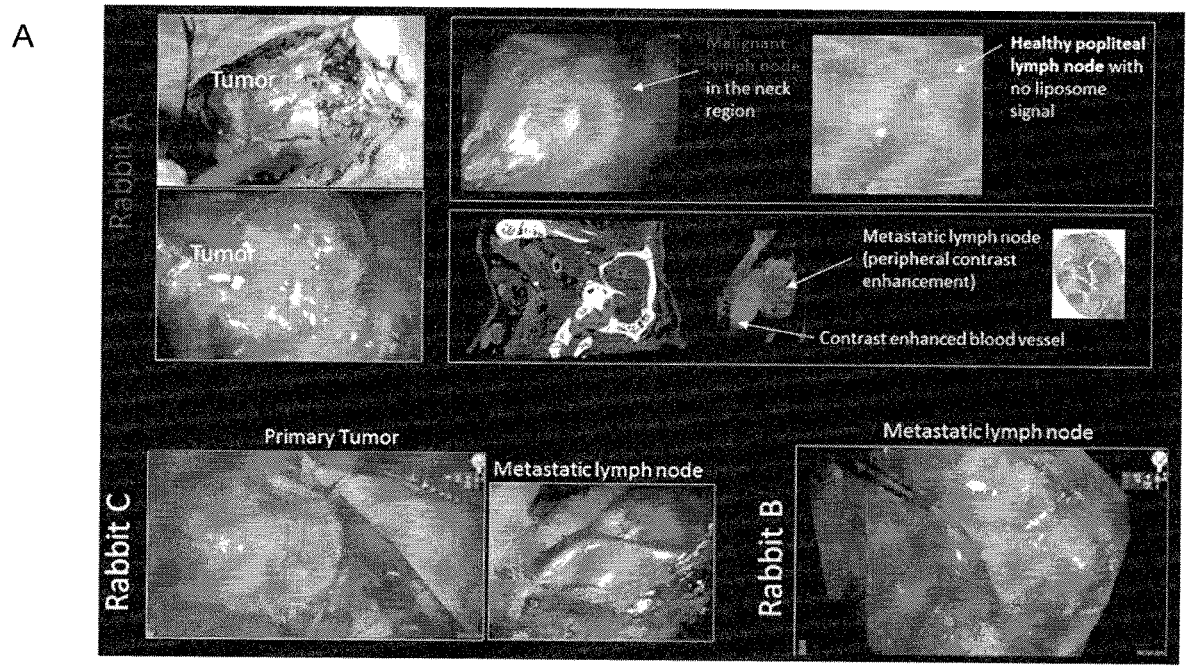
FIG. 5 shows a) Intraoperative NIR fluorescence imaging of the primary tumor and malignant lymph nodes. A control healthy lymph node (popliteal, rabbit A) was also imaged as a negative control. Feasibility demonstration of the use of CF800 for preoperative CT and intraoperative NIR fluorescence imaging of b) lymph nodes in a rabbit VX-2 buccinator muscle carcinoma model (intraoperative NIR fluorescence imaging), and c) of a small solitary pulmonary nodule (210 mm³) in a rabbit VX-2 lung cancer model in exemplary embodiments of the present application.
Figure 5:
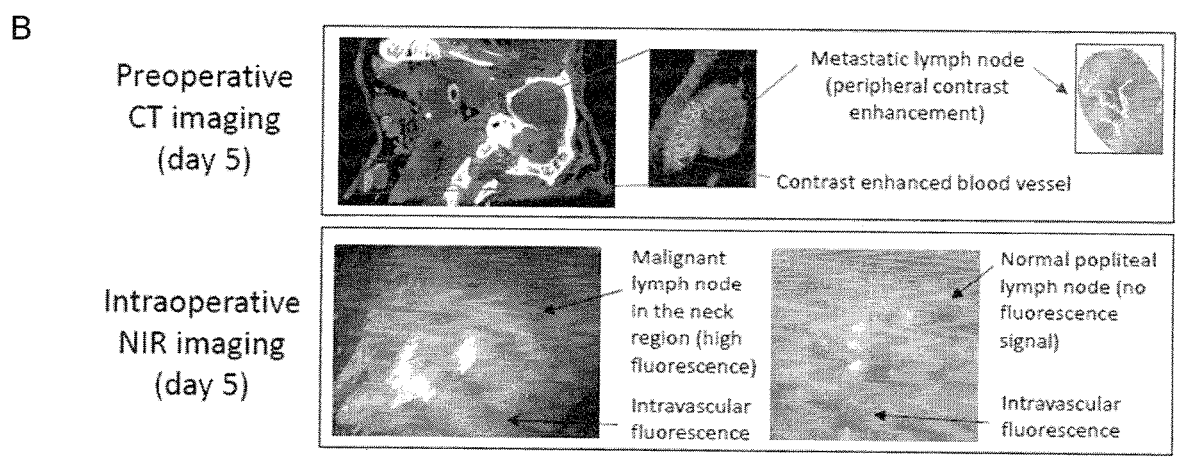
Figure 5:
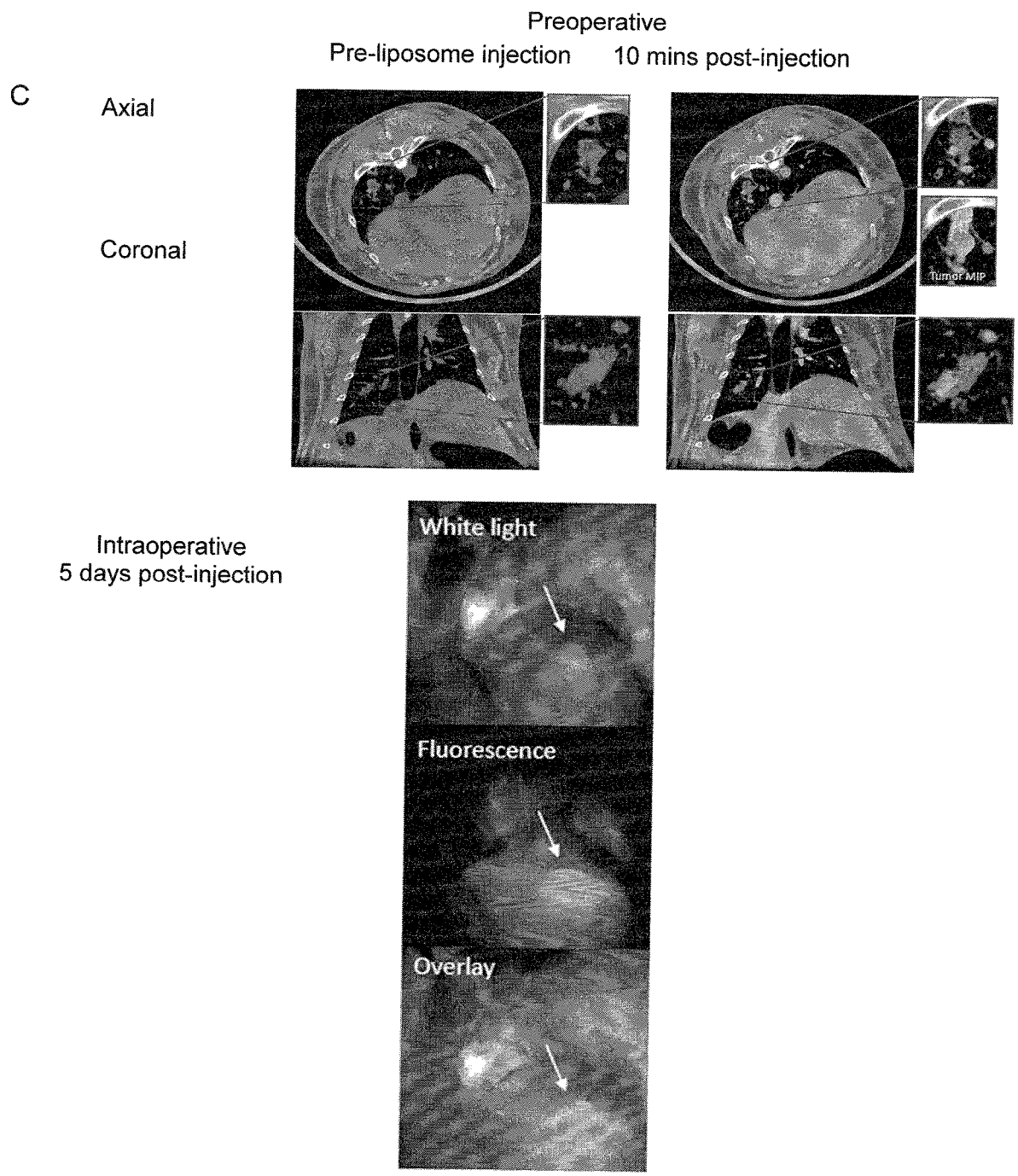
Figure 6:
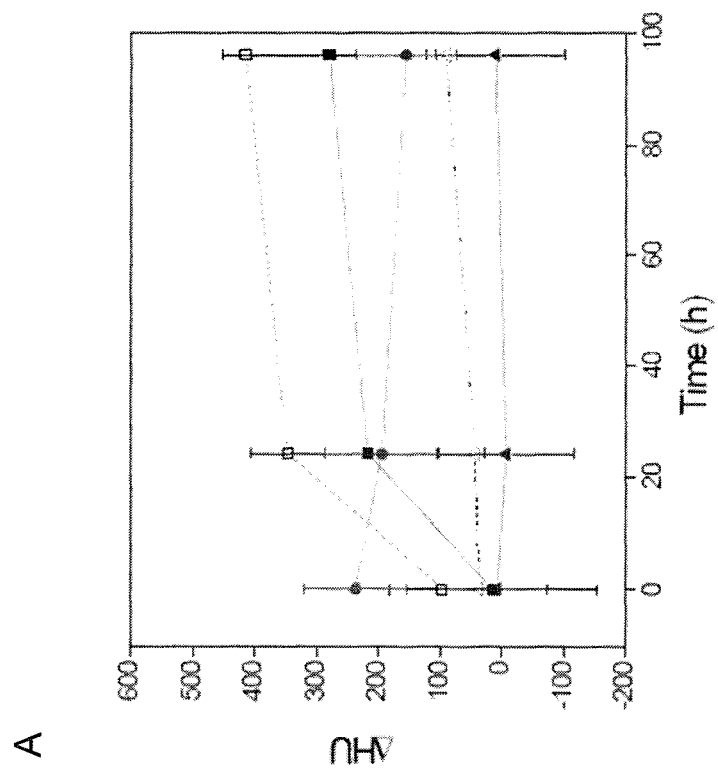
FIG. 6 shows CT-based quantification of a) mean (solid line and filled symbol) and maximum (dotted line and hollow symbol) differential signal ($\Delta HU=HU_{t=t}-HU_{t=0}$) measured from the tumor (black square), muscle (triangle) and blood (circle) over an 8-day period post-one single administration of CF800 to a rabbit bearing the VX-2 buccinator muscle carcinoma (signal measured from the same animal shown in FIG. 4b) in an exemplary embodiment of the present application. Note that the high variability measured within the tissue volumes of interest is both due to biological heterogeneity and preclinical CT scanner performance. B) In a separate phantom exemplary study, the noise levels for uniform volumes containing increasing amounts of iodine were measured using the GE Locus Ultra preclinical scanner at 80 kVp and 50 mA (black square), the clinical Siemens Flash scanner at 80 kVp and 900 mA (circle) and the clinical GE Discovery ST scanner at 120 kVp and 200 mA (triangle). This confirms that the differential signal levels achieved at the tumor site following liposome contrast administration are significantly higher than noise variations allowing for good detectability of tumor.

In the rabbit buccal mucosa tumor model, successful CT visualization of the contrast enhanced tumor (FIG. 4a) and involved lymph nodes was achieved in the pre-operative setting (FIG. 4b, top panel). Intra-operatively, NIR fluorescence imaging also demonstrated successful detection of the surgical site containing the tumor and malignant lymph nodes enhanced with CF800 (FIG. 4b, bottom panel; FIG. 5).

To explore the clinical benefit of having a single imaging agent for target visualization pre and intraoperatively, a feasibility study was conducted in collaboration with two surgical oncology groups in rabbit models of H&N and lung cancer. The intraoperative NIR fluorescence imager employed for this study is an FDA-cleared system which has been successfully used for imaging conventional ICG in patients undergoing interventional procedures [13,14]. Here, the successful use of CF800 for CT-based preoperative and NIR fluorescence-based intraoperative localization and visualization of a primary H&N tumor, a malignant cervical lymph node and a solitary pulmonary nodule was demonstrated (FIGS. 4b, 5c). More specifically, longitudinal time-course CT imaging in a representative rabbit bearing the buccal mucosa VX-2 tumor (FIG. 5b) identified significant CT contrast enhancement ($HU_{mean}$=218-280 and $HU_{max}$=347-416) at the tumor site between 24 h and 4 days post-liposome injection compared to the contralateral cheek muscle ($HU_{mean}$<12 and $HU_{max}$<91). The lowest mean tumor CT signal enhancement (in HU) is 2.7 folds higher than the highest noise level measured in the preclinical GE Locus Ultra microCT scanner (at 80 kVp and 500 mA), and 9.9 to 33.3 folds higher than the highest noise level measured in two clinical CT scanners (Siemens Flash operating at 80 kVp and 900 mA, and GE Discovery ST operating at 120 kVp and 200 mA, respectively). The high tumor signal to noise ratio estimated using clinical CT systems demonstrate feasibility for employment of CF800 for CT-based H&N tumor visualization, localization and delineation.

Figure 7:
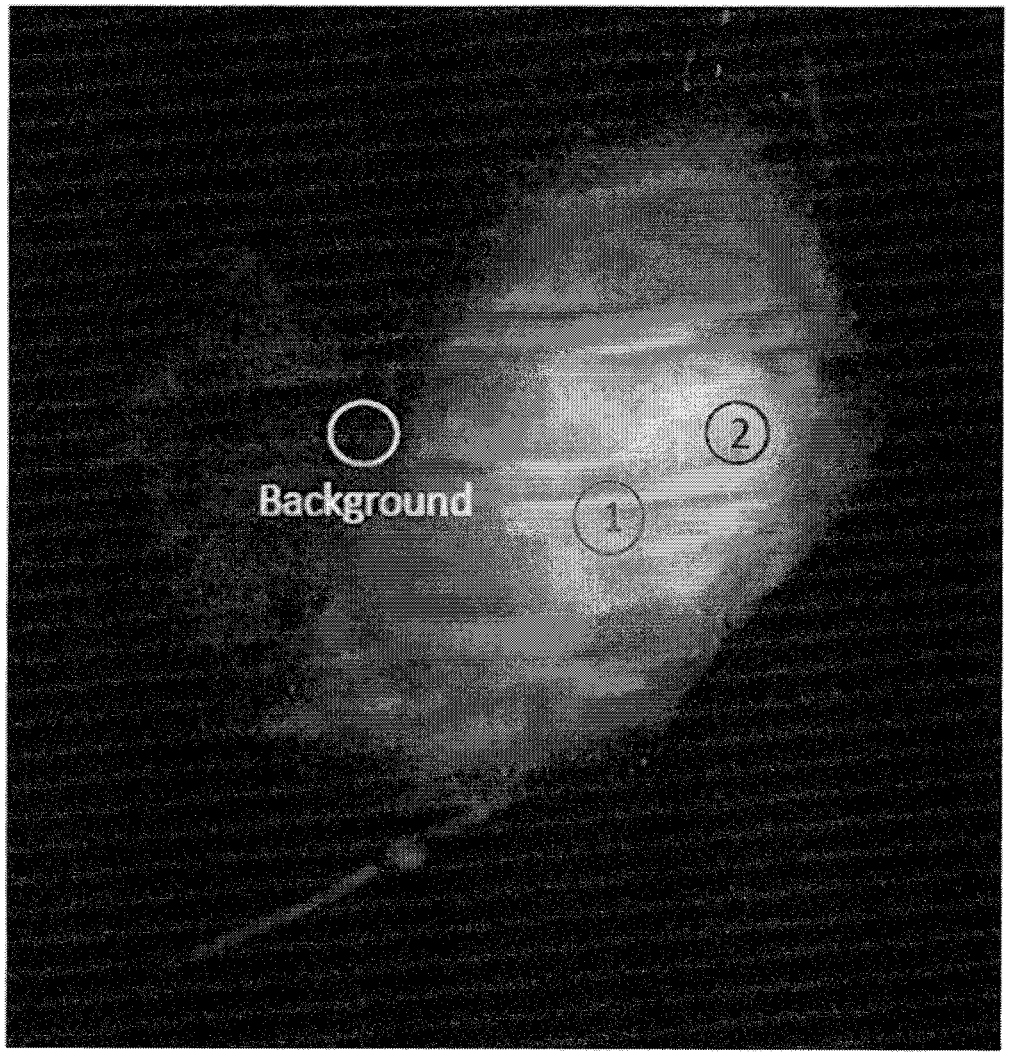
FIG. 7 shows quantification of intraoperative NIR fluorescence signal in an exemplary embodiment of the present application. In vivo NIR fluorescence-based visualization and quantification of the signal measured in arbitrary units (a.u.) from two regions of the primary tumor and a background region adjacent to the tumor over 13 video frames. The signal fluctuations are caused by motion of the fluorescence imager as it was handheld.

All surgical procedures were scheduled between day 4 and 7 post-liposome administration, based on the CT imaging results, in order to maximize the tumor-to-blood signal ratio, as high ICG signal in the blood may interfere with target lesion visualization during surgery. Intraoperatively, the mean fluorescence signal (arbitrary units) and the tumor-to-background ratio measured are highly dependent on the distance and angle between the fluorescence source and the detector. However, over the 13 frames of NIR fluorescence acquisition (FIG. 7) the fluctuations of signal intensities detected in all regions of interest were low (2.1-8.1% of the mean signal) and the difference between the signal intensities measured at the three tumor regions and the nearby background region was determined to be highly statistically significant (P<0.001).

There is evidence that this liposome imaging platform can increase the accuracy of treatment target delineation. Furthermore, it has the potential to broadly enhance the performance of image-guided cancer treatments including surgery, radiotherapy and drug delivery.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE SPECIFICATION

Coate, L. E., et al., Molecular predictive and prognostic markers in non-small-cell lung cancer. *Lancet Oncol*, 2009. 10(10): p. 1001-10.

2. Aberle, D. R., et al., Reduced lung-cancer mortality with low-dose computed tomographic screening. *N Engl J Med.* 365(5): p. 395-409.
3. Suzuki, K., et al., Video-assisted thoracoscopic surgery for small indeterminate pulmonary nodules: indications for preoperative marking. *Chest,* 1999. 115(2): p. 563-8.
4. Daly, M. J., et al., Geometric calibration of a mobile C-arm for intraoperative cone-beam CT. *Med Phys,* 2008. 35(5): p. 2124-36.
5. Siewerdsen, J. H., et al., Volume CT with a flat-panel detector on a mobile, isocentric C-arm: pre-clinical investigation in guidance of minimally invasive surgery. *Med Phys,* 2005. 32(1): p. 241-54.
6. Daly, M. J., et al., Intraoperative cone-beam CT for guidance of head and neck surgery: Assessment of dose and image quality using a C-arm prototype. *Med Phys,* 2006. 33(10): p. 3767-80.
7. Rafferty, M. A., et al., Investigation of C-arm cone-beam CT-guided surgery of the frontal recess. *Laryngoscope,* 2005. 115(12): p. 2138-43.
8. King, E., et al., Intraoperative cone-beam CT for head and neck surgery: Feasibility of clinical implementation using a prototype mobile C-arm. *Head Neck* 2013 35(7):959-67.
9. Patty, P. J. and B. J. Frisken, The pressure-dependence of the size of extruded vesicles. *Biophys J,* 2003. 85(2): p. 996-1004.
10. Hunter, D. G. and B. J. Frisken, Effect of extrusion pressure and lipid properties on the size and polydispersity of lipid vesicles. *Biophys J,* 1998. 74(6): p. 2996-3002.
11. Zheng, J., Jaffray, D. & Allen, C. Quantitative CT imaging of the spatial and temporal distribution of liposomes in a rabbit tumor model. *Mol Pharm* 6, 571-580 (2009).
12. Zheng, J., Liu, J., Dunne, M., Jaffray, D. A. & Allen, C. In vivo performance of a liposomal vascular contrast agent for CT and MR-based image guidance applications. *Pharm Res* 24, 1193-1201 (2007).
13. Reuthebuch, O., et al. Novadaq SPY: intraoperative quality assessment in off-pump coronary artery bypass grafting. *Chest* 125, 418-424 (2004).
14. Vogt, P. R., Bauer, E. P. & Graves, K. Novadaq Spy Intraoperative Imaging System—current status. *Thorac Cardiovasc Surg* 51, 49-51 (2003).
15. Zheng, J., et al. Liposome contrast agent for CT-based detection and localization of neoplastic and inflammatory lesions in rabbits: validation with FDG-PET and histology. *Contrast Media Mol Imaging* 5, 147-154.
16. Zheng, J., Perkins, G., Kirilova, A., Allen, C. & Jaffray, D. A. Multimodal contrast agent for combined computed tomography and magnetic resonance imaging applications. *Invest Radiol* 41, 339-348 (2006).
17. Munoz, R., et al. Highly efficacious nontoxic preclinical treatment for advanced metastatic breast cancer using combination oral UFT-cyclophosphamide metronomic chemotherapy. *Cancer Res* 66, 3386-3391 (2006).
18. Lin, L. M., et al. VX2-induced rabbit buccal carcinoma: a potential cancer model for human buccal mucosa squamous cell carcinoma. *Oral Oncol* 45, e196-203 (2009).
19. Anayama, T., et al. A Novel Minimally Invasive Technique to Create a Rabbit VX2 Lung Tumor Model for Nano-Sized Image Contrast and Interventional Studies. *PLoS One* 8, e67355.
20. Granton, P. V., et al. Rapid in vivo whole body composition of rats using cone beam muCT. *J Appl Physiol* 109, 1162-1169.
21. Patchen, M. L., MacVittie, T. J. & Souza, L. M. Postirradiation treatment with granulocyte colony-stimulating factor and preirradiation WR-2721 administration synergize to enhance hemopoietic reconstitution and increase survival. *Int J Radiat Oncol Biol Phys* 22, 773-779 (1992).

The invention claimed is:

1. A composition comprising an iodinated contrast agent and indocyanine green co-encapsulated inside a pegylated liposomal carrier, wherein the molar ratio of the iodinated contrast agent to indocyanine green is about 1,000:1 to about 10,000:1, wherein the liposomal carrier comprises a) one or more lipids, b) cholesterol, and c) one or more PEGylated lipids, and wherein the indocyanine green in the pegylated liposomal carrier retains at least 50% of its original fluorescence for at least 72 hours.

2. The composition of claim 1, wherein the iodinated contrast agent is iohexol.

3. The composition of claim 1, comprising an effective amount of the encapsulated iodinated contrast agent and an effective amount of encapsulated indocyanine green, wherein the effective amount of the encapsulated iodinated contrast agent is an amount effective for CT imaging in a subject and the effective amount of encapsulated indocyanine green is an amount effective for fluorescence imaging in a subject.

4. The composition of claim 1, wherein a) is a phosphatidylcholine (PC) and c) is a PEGylated phosphatidylethanolamine (PEG-PE).

5. The composition of claim 1, wherein the indocyanine green in the pegylated liposomal carrier retains at least about 70%, about 75% or about 80% of its original fluorescence for at least about 24 hours, about 48 hours, about 72 hours, about 120 hours, or about 240 hours.

6. The composition of claim 1, formulated for administration by injection or inhalation.

7. The composition of claim 1, wherein the composition emits a fluorescence signal in the near-infrared range.

8. A kit comprising the composition of claim 1 in an aqueous solution and instructions for use.

9. A kit comprising the composition of claim 1 in lyophilized form and instructions for reconstituting the composition of claim 1 in lyophilized form in an aqueous solution.

10. A method for the manufacture of the composition of claim 1, the method comprising:
 a) combining one or more neutral lipids, cholesterol and one or more PEGylated lipids with an organic solvent at a temperature of about 40° C. to about 80° C.;
 b) combining indocyanine green with a solution comprising the iodinated contrast agent at a temperature of about 20° C. to about 70° C.;
 c) mixing the combination from a) with the combination from b) under conditions to obtain multilamellar liposomes; and
 d) extruding the multilamellar liposomes at a pressure of about 50 psi to about 1000 psi to form the composition of claim 1.

11. The method of claim 10, wherein the organic solvent in a) is a $C_{1-4}$ alcohol or a chlorinated solvent.

12. The method of claim 10, wherein the temperature in a) is about 60° C. to about 80° C.

13. The method of claim 10, wherein the temperature in b) is about 30° C. to about 70° C.

14. The method of claim 10, wherein the mixing of the combination from a) with the combination from b) to obtain multilamellar liposomes is performed for at least about four hours with periodic mixing.

15. The method of claim 10, wherein the iodinated contrast agent is iohexol.

16. A method for performing one or more imaging modalities on a subject in need thereof, the method comprising administering an effective amount of a composition comprising an iodinated contrast agent and indocyanine green co-encapsulated inside a pegylated liposomal carrier, wherein the molar ratio of the iodinated contrast agent to indocyanine green is about 1,000:1 to about 10,000:1, wherein the liposomal carrier comprises a) one or more lipids, b) cholesterol, and c) one or more PEGylated lipids, and wherein the indocyanine green in the pegylated liposomal carrier retains at least 50% of its original fluorescence for at least 72 hours to the subject, and performing the one or more imaging modalities on the subject.

17. The method of claim 16, wherein the subject has cancer.

18. The method of claim 16, wherein the subject is or will be undergoing surgery.

19. The method of claim 18, wherein the surgery is a video assisted thoracic surgery (VATS), a surgery using low dose cone-beam CT imaging (CBCT), a surgery using x-ray fluoroscopy guidance, a surgery using CT image-guidance, a surgery using dual-energy CT image-guidance, a surgery using optical image-guidance or any other surgical procedure where the composition modifies imaging signal and/or contrast.

* * * * *